(12) United States Patent
Er (10) Patent No.: US 12,305,662 B2
(45) Date of Patent: May 20, 2025

(54) CONVEYING BLADES FOR A COMPRESSIBLE ROTOR

(71) Applicant: ECP Entwicklungsgesellschaft mbH, Aachen (DE)

(72) Inventor: Sami Er, Aachen (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 0 days.

(21) Appl. No.: 18/885,089

(22) Filed: Sep. 13, 2024

(65) Prior Publication Data

US 2025/0084864 A1    Mar. 13, 2025

Related U.S. Application Data

(63) Continuation of application No. 18/238,564, filed on Aug. 28, 2023, now Pat. No. 12,117,014, which is a
(Continued)

(30) Foreign Application Priority Data

Dec. 23, 2009   (EP) ..................... 09075571

(51) Int. Cl.
*A61M 60/205*   (2021.01)
*A61M 60/13*    (2021.01)
(Continued)

(52) U.S. Cl.
CPC ........... *F04D 29/247* (2013.01); *A61M 60/13* (2021.01); *A61M 60/135* (2021.01);
(Continued)

(58) Field of Classification Search
CPC .. A61M 1/101; A61M 1/1024; A61M 1/1034; A61M 1/125; A61M 5/142;
(Continued)

(56) References Cited

U.S. PATENT DOCUMENTS 3,510,229 A   5/1970   Smith
3,568,659 A   3/1971   Karnegis
(Continued)

FOREIGN PATENT DOCUMENTS

CA   1008330 A    4/1977
CA   2311977 A1   12/2000
(Continued)

OTHER PUBLICATIONS

International Search Report and Written Opinion for International Application No. PCT/EP2010/007998 dated Mar. 15, 2011 (8 pp.).
(Continued)

*Primary Examiner* — Aaron R Eastman
(74) *Attorney, Agent, or Firm* — BOTOS CHURCHILL IP LAW LLP (57) ABSTRACT

To provide a simple embodiment of a rotor for a fluid pump which is nevertheless very flexible in handling and compressible, in accordance with the invention a conveying blade is provided having at least two struts and a membrane spanned between them in the expanded state, wherein the struts each have at least one joint, in particular more than one joint, which enables an angling in a first direction in a first movement plane and bounds an overelongation beyond an elongation angle of in particular 180° in the opposite second direction. In particular when a plurality of joints are provided at the struts, they, and with them the conveying blades, are particularly flexible for simple compressibility.

15 Claims, 4 Drawing Sheets

Related U.S. Application Data continuation of application No. 18/079,995, filed on Dec. 13, 2022, now Pat. No. 11,773,863, which is a continuation of application No. 17/590,531, filed on Feb. 1, 2022, now Pat. No. 11,549,517, which is a continuation of application No. 17/023,837, filed on Sep. 17, 2020, now Pat. No. 11,266,824, which is a continuation of application No. 16/037,758, filed on Jul. 17, 2018, now Pat. No. 10,806,838, which is a continuation of application No. 15/069,627, filed on Mar. 14, 2016, now Pat. No. 10,052,419, which is a continuation of application No. 13/261,319, filed as application No. PCT/EP2010/007998 on Dec. 23, 2010, now Pat. No. 9,314,558.

(60) Provisional application No. 61/289,645, filed on Dec. 23, 2009.

(51) Int. Cl.
| | |
|---|---|
| *A61M 60/135* | (2021.01) |
| *A61M 60/174* | (2021.01) |
| *A61M 60/216* | (2021.01) |
| *A61M 60/414* | (2021.01) |
| *A61M 60/808* | (2021.01) |
| *F04D 29/18* | (2006.01) |
| *F04D 29/24* | (2006.01) |
| *F04D 29/60* | (2006.01) |
| *A61M 60/148* | (2021.01) |

(52) U.S. Cl.
CPC ........ *A61M 60/174* (2021.01); *A61M 60/205* (2021.01); *A61M 60/216* (2021.01); *A61M 60/414* (2021.01); *A61M 60/808* (2021.01); *F04D 29/181* (2013.01); *F04D 29/607* (2013.01); *A61M 60/148* (2021.01)

(58) Field of Classification Search
CPC .......... A61M 5/14236; A61M 5/14276; A61M 1/122; A61M 60/205; A61M 60/135; A61M 60/414; A61M 90/148; A61M 60/808; A61M 60/13; A61M 60/174; A61M 60/216; A61M 60/148; F04D 29/181; F04D 29/607; F04D 29/247
USPC .......... 416/87, 88, 223 R, 240, 142; 604/22; 403/300, 301
See application file for complete search history.

(56) References Cited

U.S. PATENT DOCUMENTS

| | | |
|---|---|---|
| 3,802,551 A | 4/1974 | Somers |
| 3,812,812 A | 5/1974 | Hurwitz |
| 4,014,317 A | 3/1977 | Bruno |
| 4,207,028 A | 6/1980 | Ridder |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | Mckenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,151,721 A | 9/1992 | Allendorf et al. |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,749,855 A | 5/1998 | Reitan |
| 5,755,784 A | 5/1998 | Jarvik |
| 5,776,190 A | 7/1998 | Jarvik |
| 5,813,405 A | 9/1998 | Montano et al. |
| 5,820,571 A | 10/1998 | Erades et al. |
| 5,851,174 A | 12/1998 | Jarvik et al. |
| 5,877,566 A | 3/1999 | Chen |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Schmitz-rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nuesser et al. |
| 6,790,171 B1 | 9/2004 | Gruendeman et al. |
| 6,860,713 B2 | 3/2005 | Hoover |
| 6,945,977 B2 | 9/2005 | Demarais et al. |
| 6,981,942 B2 | 1/2006 | Khaw et al. |
| 7,022,100 B1 | 4/2006 | Aboul-hosn et al. |
| 7,027,875 B2 | 4/2006 | Siess et al. |
| 7,054,156 B2 | 5/2006 | Espinoza-ibarra et al. |
| 7,074,018 B2 | 7/2006 | Chang |
| 7,179,273 B1 | 2/2007 | Palmer et al. |
| 7,393,181 B2 | 7/2008 | Mcbride et al. |
| 7,467,929 B2 | 12/2008 | Nuesser et al. |
| 7,731,675 B2 | 6/2010 | Aboul-hosn et al. |
| 7,841,976 B2 | 11/2010 | Mcbride et al. |
| 7,927,068 B2 | 4/2011 | Mcbride et al. |
| 7,934,909 B2 | 5/2011 | Nuesser et al. |
| 8,079,948 B2 | 12/2011 | Shifflette |
| 2002/0094273 A1 | 7/2002 | Huang |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2005/0101200 A1 | 5/2005 | Townsend |

(56) References Cited

U.S. PATENT DOCUMENTS

| | | |
|---|---|---|
| 2006/0008349 A1 | 1/2006 | Khaw |
| 2006/0062672 A1 | 3/2006 | Mcbride et al. |
| 2006/0195004 A2 | 8/2006 | Jarvik |
| 2007/0270875 A1 | 11/2007 | Bacher et al. |
| 2008/0073983 A1 | 3/2008 | Krajcir |
| 2008/0103591 A1 | 5/2008 | Siess |
| 2008/0114339 A1 | 5/2008 | Mcbride et al. |
| 2008/0132747 A1 | 6/2008 | Shifflette |
| 2008/0132748 A1* | 6/2008 | Shifflette ............ A61M 60/865 600/16 |
| 2008/0262584 A1 | 10/2008 | Bottomley et al. |
| 2008/0306327 A1 | 12/2008 | Shifflette |
| 2009/0060743 A1 | 3/2009 | Mcbride et al. |
| 2009/0062597 A1 | 3/2009 | Shifflette |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0268017 A1 | 10/2010 | Siess |
| 2011/0071338 A1 | 3/2011 | Mcbride et al. |
| 2011/0236210 A1 | 9/2011 | Mcbride et al. |
| 2011/0238172 A1 | 9/2011 | Akdis |
| 2011/0257462 A1 | 10/2011 | Rodefeld et al. |
| 2011/0275884 A1 | 11/2011 | Scheckel |
| 2012/0039711 A1 | 2/2012 | Roehn |
| 2012/0039713 A1 | 2/2012 | Shifflette |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 A1 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 | 12/1994 |
| DE | 19535781 A1 | 3/1997 |
| DE | 19711935 A1 | 4/1998 |
| DE | 29804046 U1 | 4/1998 |
| DE | 69407869 T2 | 4/1998 |
| DE | 69017784 T3 | 4/2000 |
| DE | 69427390 T2 | 9/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 0480102 A1 | 4/1992 |
| EP | 0560000 A2 | 9/1993 |
| EP | 0629412 A2 | 12/1994 |
| EP | 0768091 A1 | 4/1997 |
| EP | 0884064 A2 | 12/1998 |
| EP | 0914171 A2 | 5/1999 |
| EP | 0916359 A1 | 5/1999 |
| EP | 951302 A2 | 10/1999 |
| EP | 1019117 A1 | 7/2000 |
| EP | 1066851 A1 | 1/2001 |
| EP | 1114648 A2 | 7/2001 |
| EP | 1337288 A1 | 8/2003 |
| EP | 1651290 A1 | 5/2006 |
| EP | 2047872 A1 | 4/2009 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| GB | 2405677 A | 3/2005 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 94001148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 9944651 A1 | 9/1999 |
| WO | 0027446 A1 | 5/2000 |
| WO | 0043054 A2 | 7/2000 |
| WO | 0062842 A1 | 10/2000 |
| WO | 2001007760 | 2/2001 |
| WO | 2001007787 | 2/2001 |
| WO | 2001083016 A2 | 11/2001 |
| WO | 2003057013 | 7/2003 |
| WO | 2003103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006051023 A1 | 5/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | 2009029959 A2 | 3/2009 |
| WO | 2009073037 A1 | 6/2009 |
| WO | 2010133567 A1 | 11/2010 |
| WO | 2013034547 A1 | 3/2013 |

(56) References Cited

FOREIGN PATENT DOCUMENTS

| | | |
|---|---|---|
| WO | 2013092971 A1 | 6/2013 |
| WO | 2013093001 A2 | 6/2013 |
| WO | 2013093058 A1 | 6/2013 |

OTHER PUBLICATIONS

Office Action from corresponding DE Application No. 11 2010 004 979.3 dated May 16, 2022, (13 pp.).

\* cited by examiner

CONVEYING BLADES FOR A COMPRESSIBLE ROTOR

CROSS REFERENCE TO RELATED APPLICATIONS

The present application is a continuation of U.S. patent application Ser. No. 18/238,564, filed Aug. 28, 2023, now U.S. Pat. No. 12,117,014, which is a continuation of U.S. patent application Ser. No. 18/079,995, filed Dec. 13, 2022, now U.S. Pat. No. 11,773,863, which is a continuation of U.S. patent application Ser. No. 17/590,531, filed Feb. 1, 2022, now U.S. Pat. No. 11,549,517, which is a continuation of U.S. patent application Ser. No. 17/023,837, Sep. 17, 2020, now U.S. Pat. No. 11,266,824, which is a continuation of U.S. patent application Ser. No. 16/037,758, filed Jul. 17, 2018, now U.S. Pat. No. 10,806,838, which is a continuation of U.S. patent application Ser. No. 15/069,627, filed Mar. 14, 2016, now U.S. Pat. No. 10,052,419, which is a continuation of U.S. patent application Ser. No. 13/261,319, filed Aug. 8, 2012, now U.S. Pat. No. 9,314,558, which is a national phase entry under 35 U.S.C. § 371 of International Application No. PCT/EP2010/007998, filed Dec. 23, 2010, published as International Publication No. WO 2011/076441, which claims the benefit of the filing date of U.S. Provisional Application No. 61/289,645, filed Dec. 23, 2009, and European Patent Application No. 09075571.1, filed Dec. 23, 2009, the disclosures of which are hereby incorporated herein by reference.

TECHNICAL FIELD

The invention is in the field of mechanical engineering, in particular microengineering, and relates to conveying blades for rotors of fluid pumps which are particularly suitable for use in areas which are difficult to access.

BACKGROUND

Such pumps can be configured so small as micropumps in medical engineering, for example, that they can be introduced into blood vessels with microinvasiveness. They can then be used for assisting the pumping force of the human heart.

To make such pumps advantageously deployable, they are often designed compressible and expandable so that they can be introduced in a compressed state through a blood vessel, for example up to and into a ventricle, and can be expanded there.

Provision is often made for this purpose that a corresponding rotor of the pump which can be driven very fast in operation is radially changeable, i.e., compressible and expandable between the transport state and the operating state.

Similar applications are, however, also conceivable in the non-medical area with larger pumps which should be used in regions difficult to access.

A plurality of such pumps are already known, with different principles being used to achieve compressibility. It is known from WO 98/53864 to use an axial flow pump having a rotor, wherein the rotor has the form of a rigid tube which is externally journaled in a stator. In this respect, the drive can be directly integrated into the stator and the rotor as an electromagnetic drive.

A pump having a compressible rotor is, in contrast thereto, known from WO 03/103745 A2, wherein the rotor with this pump has an unfoldable rotor blade which unfolds in operation due to the fluid pressure of the blood.

A pump is known in WO 2006/051023 having a rotor which has two cover surfaces and centrifugal blades disposed therebetween. The cover surfaces are pivotably fastened to the hub by means of joints.

BRIEF SUMMARY

It is the underlying object of the present invention with regard to the prior art to provide a rotor or a conveying blade for a rotor which are compressible and expandable and, in this respect, have a construction design which is as simple as possible, are reliable and durable as well as inexpensive in manufacture.

The object is satisfied by the features of the invention.

In this respect, a corresponding conveying blade has at least two struts as well as a membrane held between them in the expanded state of the rotor or in the elongated state of the struts, and the struts in turn each have at least one joint, in particular more than one joint, which allows an angling in one direction in a first movement plane and bounds an overelongation beyond an elongation angle, in particular 180°, in the opposite second direction within the first movement plane. The elongation angle can also be less than 180°, for example 170°, 160° or 180°, or more than 180°, for example 190°, 200° or 210°, if a strut is intended to be realized which is curved in the operating state. The elongation angle of mutually adjacent joints can be equal, but can also vary. In this respect, a further deformation beyond the elongation angle can moreover be possible in operation by mechanical strain on the struts by a fluid counter-pressure while utilizing the elasticity of the strut sections and the inherent elasticity of the joint material, with the force required for a further deformation/elongation, however, rising steeply on a reaching of the elongation angle.

The joint or joints are in this respect arranged over the length of the individual struts and are at least partly spaced apart from the hub such that they separate different sections of the struts from one another and allow the mutual angling of the individual sections. The conveying blade can thereby be easily folded or rolled up.

In this respect, at least one joint is spaced apart from a hub of the rotor, for example by at least the radius or twice the radius of the hub.

All of the joints, or at least the majority of joints, are advantageously kinkable in the same direction of movement so that the total conveying blade can be rolled up.

Such a joint kinkable in one direction is in particular at least further pivotable in this first direction than in the opposite second direction within the same movement plane. The movability of a joint is thus asymmetrically bounded in the two opposite directions starting from the elongated position.

In the rolled-up state, the conveying blade or the rotor to which it is fastened thus has a small radial extent and can thus easily be brought to the operating site.

Alternatively, adjacent joints can also be able to be angled in opposite directions to enable a concertina-like folding together. It is important in this respect that all the joints of the struts are brought into a defined, elongated position by the fluid counter-pressure and are stabilized there. The named joints are generally advantageously, but not necessarily, configured as flexural hinges, integral hinges or hinge joints.

After being brought to the operating site/deployment site, the rotor can be driven so that the conveying blade or a plurality of conveying blades are erected by centrifugal forces and/or by a fluid counter-pressure which is adopted.

In a modified embodiment, the unfolding of the rotor can also be realized by elastic restoring forces in the joints. The elastic restoring forces can also become effective in combination with centrifugal forces or fluid counter-pressure.

The active area of the conveying blade or conveying blades is thus increased so that the corresponding fluid pump has a good efficiency in operation.

To stabilize the respective conveying blade in expanded form in the deployed state, provision is made that the individual joints bound an overelongation of the strut or of the mutually adjacent sections beyond the elongation angle. In this respect, the respective joint can also be able to be elongated elastically some degrees beyond 180°, but advantageously no more than 200°. The conveying blade can thus, for example, react with elastic yielding to impact strains in operation.

A plurality of joints, for example two, more than five, more than ten or more than twenty joints, are advantageously provided at each of the struts to facilitate a smooth rolling up, folding up or compressing of the conveying blades.

The different struts can be mutually connected to one another by further struts which facilitate an opening of the conveying blades and can hold the membrane spanned. These connection struts can in turn be connected to the joints.

At least two struts, in particular also three struts, can advantageously be arranged parallel to one another or in fan shape starting from a common base. An ergonomically favorable conveying blade which can be fastened to a hub of a rotor can thus easily be designed from two or more struts. The conveying blade can, for example, have the form of an airplane propeller blade overall.

The individual struts can advantageously start from a common point in the region of the hub, expand the conveying blade radially outwardly in the manner of a fan and, optionally, converge again radially outwardly toward the tip of the conveying blade or be connected to one another there by a transverse strut.

Provision can, however, also be made that the struts are fastened to an arc segment in the region of the hub, for example to an arc segment of a circle or to an elliptical arc segment or to a ring which is outwardly fastened to the hub. Different arc segments of a circle of different conveying blades can then be combined to a circular ring which can easily be pushed onto a hub of a rotor.

Provision can moreover advantageously be made that the first movement plane which corresponds to an expanded state of the rotor in the maximum elongated state of the joints extends parallel to a common plane of the struts or tangentially to the membrane spanned between the struts in the region of said struts. In this case, the conveying blade can easily be flipped together or folded together or rolled up in the plane of the membrane or tangentially to the membrane surface and can be rolled up around the hub in the compressed state of the rotor, for example in the peripheral direction.

Provision can be made alternatively to this that the first movement plane which corresponds to an expanded state of the rotor in the maximum elongated state of the struts extends substantially perpendicular to a common plane of the struts or extends perpendicular to the membrane spanned between the struts in the region of said struts. In this case, each of the conveying blades can be rolled up, flipped over or folded perpendicular to the plane of the blade surface so that the conveying blades can, for example, be laid against the hub parallel thereto in the longitudinal direction to minimize the radial extent of the rotor.

The individual joints prevent a corresponding compression movement in the respective direction opposed to the kinking so that the conveying blades are stabilized in operation.

A folding together of the respective rotor can, for example, thereby take place or be supported in that the rotor is braked or is moved against the operating direction during pumping. Provision can be made that the joints are biased such that they are only held in the elongated state in operation by the fluid counter-pressure or the centrifugal force so that the rotor or the conveying blades automatically roll up when the rotor is stationary.

An advantageous embodiment of the invention provides that at least one joint has a support element at which at least one section of a strut is rotatably mounted and two adjacent sections are supported in the elongated state. The respective support element can be configured, for example, as a plate having a bearing block at which a respective section of a strut is mounted so that it is kinkable in a first direction with respect to the support element or with respect to a second section of the strut, but can only be angled in a second movement direction up to the elongation angle, for example, not substantially more than 180° into an elongated position of the strut. In this respect, in dependence on the position of the bearing block or the bearing point, the respective section can in each case abut the support element to bound the elongation movement either on the side of the bearing facing the second section or on the side of the bearing remote from the second section.

The support element can advantageously be structured symmetrically with respect to a center plane between two sections mutually adjacent at the joint. The support element can moreover comprise a material which is more elastic than the material of the strut.

A further advantageous embodiment of the invention provides that a first section of the strut is pivotably journaled at a second section of the strut in a bearing of a joint such that the two sections partly overlap in the longitudinal direction in the elongated position and that the first section has a pivot lever on a first side of the bearing and a support lever on the other side of the bearing, with the support lever being supported at the second section in the elongated state of the joint.

In the elongated state of the strut, the two mutually adjacent sections are approximately parallel to one another and are supported on one another such that the first section is mounted in a bearing fastened to the second section and has a pivot lever on the one side of the bearing and a support lever on the oppositely disposed side of the bearing, with the support lever being supported at the second section in the elongated state. In the opposite direction, the pivot lever is freely pivotable and the support lever is distanced from the point at which it is supported at the second section in the elongated state.

Alternatively, to this, provision can also be made that a first section of the strut is mounted at a second section of the strut in the bearing of a joint such that the two sections partly overlap in the longitudinal direction in the elongated position and that the first section has a pivot lever on a first side of the bearing and a support lever on the second side of the bearing, with the pivot lever being supported at the end of the second section in the elongated state. In this case, the pivot lever is in turn supported at the second section and is freely movable in the opposite direction in the elongated state.

A further advantageous embodiment of the invention provides that a first section of the strut and a second section of the strut are arranged adjacent to one another at the end face in the elongated state and are connected to one another by means of an asymmetrical film hinge.

The two sections can generally be kinked with respect to one another with respect to the angle enclosed between them by the provision of a film hinge. It is ensured by the asymmetrical design of the film hinge that the kinking is possible in a first direction, but is bounded in a second direction in the elongated state of the strut.

Provision can specifically be made for this purpose that the film hinge is arranged at the side of the strut disposed inwardly in the compressed state of the rotor and in the kinked state of the strut where the sections of the strut kinked with respect to one another include the smaller angle with one another and that each of the sections forms an abutment at the outwardly disposed side of the strut, with the abutments contacting one another in the elongated state of the strut.

The inwardly disposed side of the strut means the side which has an angle less than 180° in the compressed state of the conveying blade. In this region, different mutually adjacent sections of the strut can be folded toward one another. The opposite side of the strut with respect to its longitudinal axis or longitudinal plane is called the outer side.

A corresponding film hinge can either comprise a different material than the sections and can be connected to both sections, for example by adhesive bonding, welding or other joining techniques, or the film hinge can comprise the same material as the sections and also be contiguous thereto in one piece.

It is, for example, possible in this case to provide the film hinge by introduction of a cut-out at the outer side of the strut. Such a cut-out can, for example, be introduced by laser cutting, etching or other erosion techniques. The corresponding cut-out can be introduced as a straight section or also as a wedge-shaped cut-out or in another form. The size of the cut-out determines when the two sections of the strut abut one another at the outer side disposed opposite the film hinge on a movement of the strut in the elongation direction and thus bound an overelongation.

In another alternative of the embodiment of a joint, provision can also be made that the first and second sections of the strut are connected to one another at the end face by means of a joint section which comprises a material at the inner side of the strut at least up to the center plane of the strut which is more easily compressible than the material on the outer side of the strut. A separate joint section is then provided which has a different structure on the inner side and outer side of the strut, for example is comprised of different materials. The material on the inner side of the strut is advantageously easily compressible, at least more easily compressible than on the outer side of the strut. The material located at the outer side of the strut can be designed as stretchable, as hard as possible and non-compressible. With good compressibility, the material on the inner side of the strut (which is therefore more compressible than on the outer side) can be configured as highly tensile, for example can be reinforced through highly tensile fibers.

Provision can also be made that the strut is coated on the outside in the joint region with a material which is harder than the material of the joint section.

The invention also relates, in addition to a conveying blade for a compressible rotor, to a rotor for a fluid pump which is provided with corresponding conveying blades. The invention furthermore also relates to a corresponding fluid pump, in particular to a blood pump for the medical area, which is equipped with a corresponding compressible rotor or compressible conveying blades in accordance with the invention.

BRIEF DESCRIPTION OF DRAWINGS

The invention will be shown and subsequently described in the following with reference to an embodiment in a drawing. There are shown FIG. 1 generally, the use of a blood pump in accordance with the invention with a compressible rotor in a ventricle.

DETAILED DESCRIPTION

Figure 1:
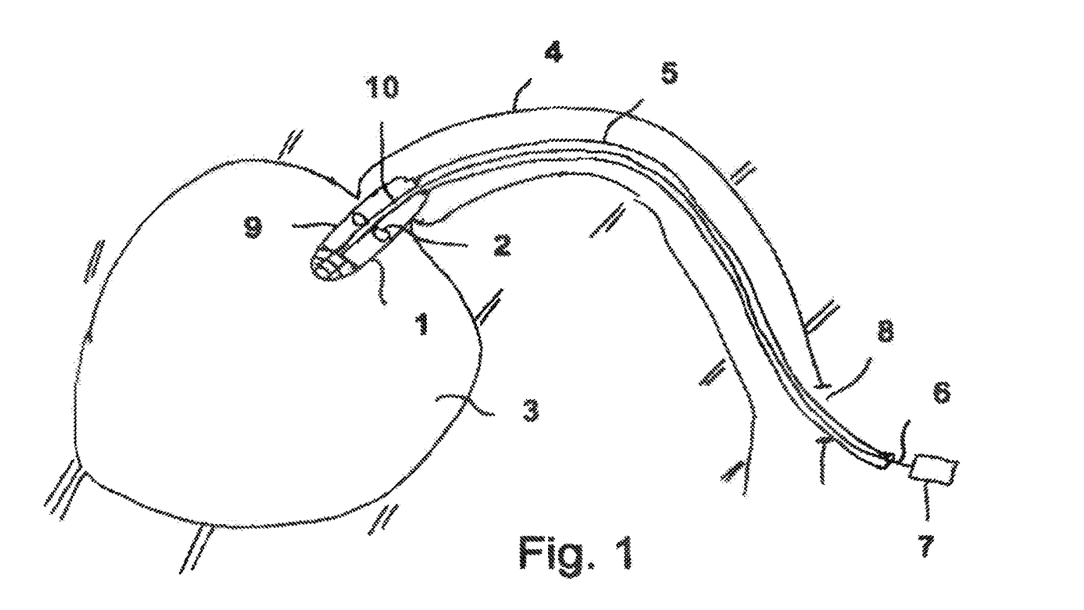

FIG. 1 shows a heart pump 1 which is located at its deployment site in the interior of a ventricle 3 and has a rotor 2 which has conveying blades on a hub 10 and is arranged inside a pump housing 9. The pump housing 9 is located at the transition from a blood vessel 4 to the ventricle 3. The pump is able to suck blood out of the ventricle 3 and to convey it into the blood vessel 4.

The pump 1 is arranged at the end of a hollow catheter 5 which is introduced through a sluice 8 into the body of a patient or into the blood vessel 4 and which accommodates a shaft 6 in its interior which can be driven at high speeds and is connected to the hub 10 within the pump. The shaft 6 is connected to a motor 7 at its proximal end at the drive side.

To transport the pump 1 through the blood vessel, it can be radially compressed in order then to be radially expanded after being brought into the ventricle 3 and to achieve a correspondingly improved efficiency or the desired pump performance.

Figure 2:
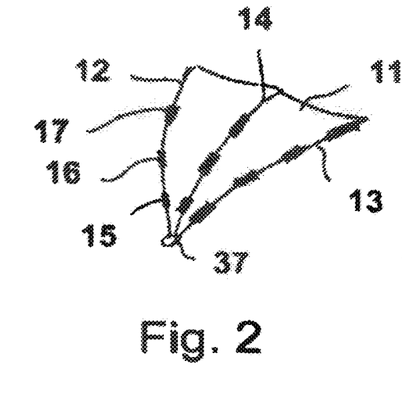
FIG. 2 schematically, the structure of a conveying blade with three struts arranged in fan shape.

FIG. 2 shows by way of example a conveying blade 11 of the rotor 2 in accordance with the invention in which a membrane is spanned between three struts 12, 13, 14 and is fastened to the individual struts, for example, by means of adhesive bonding, welding or in a similar manner.

The membrane can also be attached simply by dipping the struts into a liquid plastic, for example polyurethane. The struts 12, 13, 14 each have a plurality of joints 15, 16, 17 of which three or four are respectively shown at the individual struts.

The struts 12, 13, 14 converge at their base at a point 37 in which they are fastened to a hub 10.

The nature of the joints 15, 16, 17 will be looked at in more detail further below.

Figure 3:
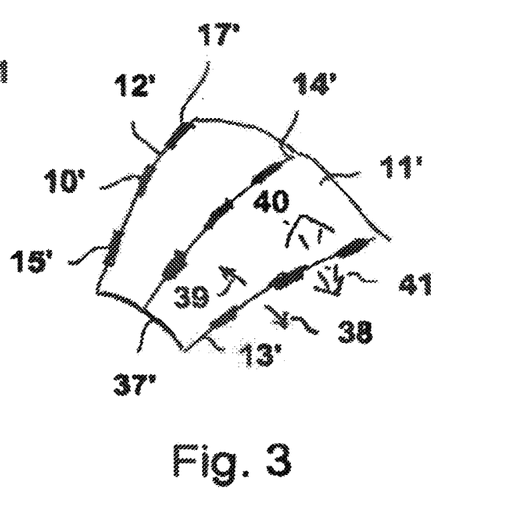
FIG. 3 the structure of a conveying blade with a base in the shape of a circle segment.

FIG. 3 shows a modified construction of a conveying blade 11' with struts 12', 13', 14' which each have joints 15', 16', 17' and which converge at a base 37' which is configured in the form of a segment of an arc of a circle and can be fastened to a correspondingly formed hub 10 of a rotor.

The movement plane which is aligned within the plane of the struts 12', 13', 14' or tangentially to the membrane at the respective point is shown by the arrows 38, 39 in FIG. 3.

The directions perpendicular to the corresponding plane of the membrane or of the tangential surface of the membrane at the respective point are indicated by the arrows 40, 41.

Figure 4:
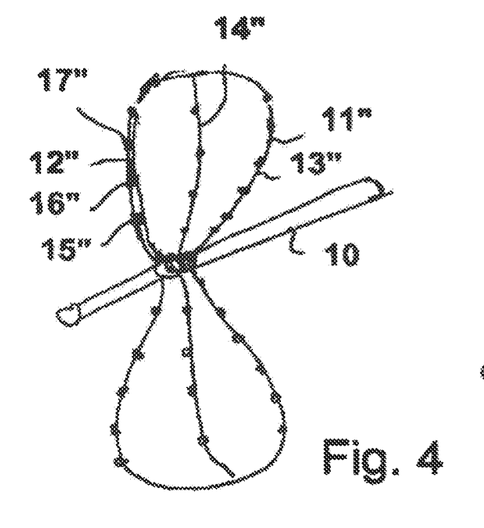
FIG. 4 a view of a rotor in expanded form.

FIG. 4 shows two conveying blades of which the upper one is marked by 11" and is shown in more detail. The two conveying blades are fastened radially opposite to one another, symmetrically at a hub 10. The conveying blade 11" has struts 12", 13" between which a membrane is spanned, with each of the struts as well as a third strut 14" disposed between them having joints 15", 16", 17" which are kinkable in the plane perpendicular to the surface of the conveying blade 11" or at the respective struts perpendicular to the membrane surface or to the tangent of the membrane surface.

Figure 5:
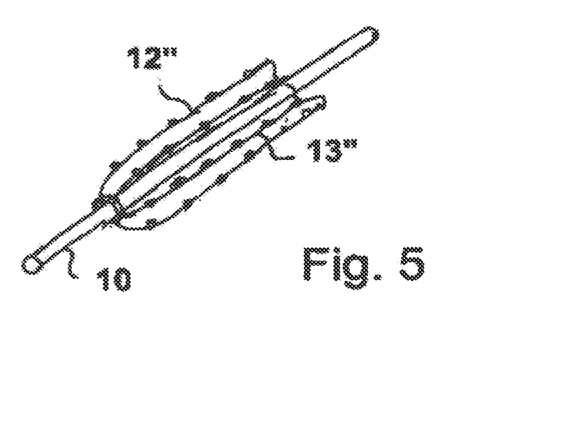
FIG. 5 a view of the rotor of FIG. 4 in compressed form.

In this way, the individual conveying blades 11" can be folded onto the hub 10 in the axial direction thereof as is shown in FIG. 5 in the compressed state of the rotor with reference to the struts 12" and 13".

The struts 12", 13" are radially erected in operation by centrifugal forces by rotation of the hub, driven by the shaft 6 shown in FIG. 1.

Figure 6:
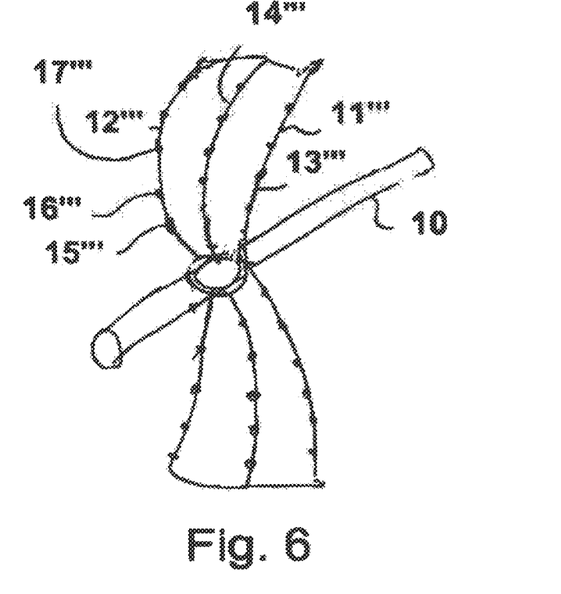
FIG. 6 a view of a further rotor in expanded form.

FIG. 6 shows a further rotor having two conveying blades of which the upper one is marked by 11'''. It has struts 12''', 13''', 14''' which are provided with respective joints 15''', 16''', 17'. The joints are each kinkable in a first movement direction within the plane of the conveying blade, i.e., parallel to the membrane in the region of the respective strut or to a tangential surface of the membrane so that the conveying blades 11''' can be flipped or folded onto the hub 10 in the peripheral direction.

Figure 7:
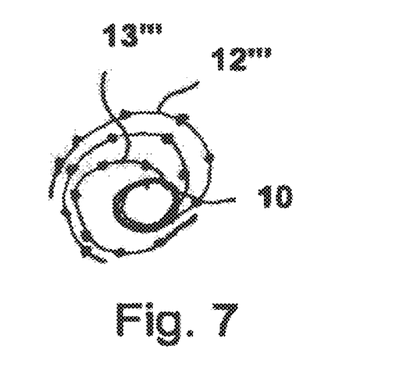
FIG. 7 a view of the rotor of FIG. 6 in compressed form.

In the compressed state, the struts 12''', 13''' lie about the hub 10, as is shown in more detail in FIG. 7.

Figure 8:
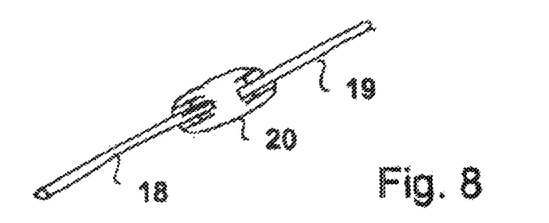
FIG. 8 a schematic view of a joint of a strut.

FIG. 8 shows the construction of the joints in a first embodiment in more detail, with a support element 20 being shown in the form of a plate between two sections 18, 19 of a strut. The support element 20 has two bearing blocks 21, 22 which are shown in more detail in a side view in FIG. 9 and in which a respective bearing shaft 21', 22' is journaled. The sections 18, 19 are rotatably journaled on the corresponding shafts.

Figure 9:
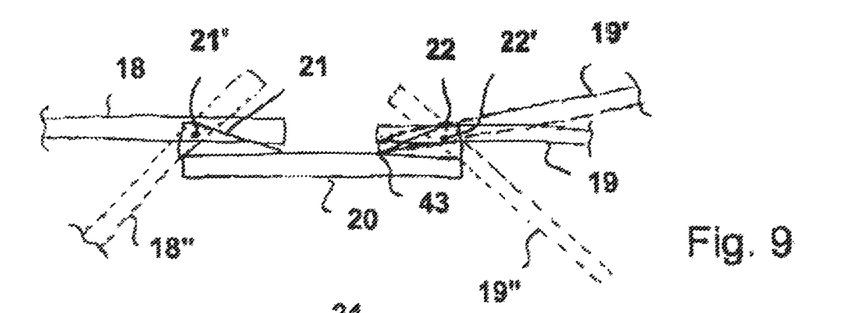
FIG. 9 the joint of FIG. 8 in different states, schematically.

The section 19 is additionally shown by dashed lines in the overelongated position 19' on the right-hand side of the support element 20 and the second is supported at this position at the point marked by 43 at the support element 20, whereby a further angling of the section 19 with respect to the section 18 is prevented.

The section 19 on the right-hand side is marked by 19" in the kinked position which is likewise shown by dashed lines. The corresponding strut is angled or folded with the sections 18, 19 in this kinked position so that the rotor adopts a compressed position. Only the angled position of section 18 is shown by 18" at the left-hand side.

Figures 10, 11:
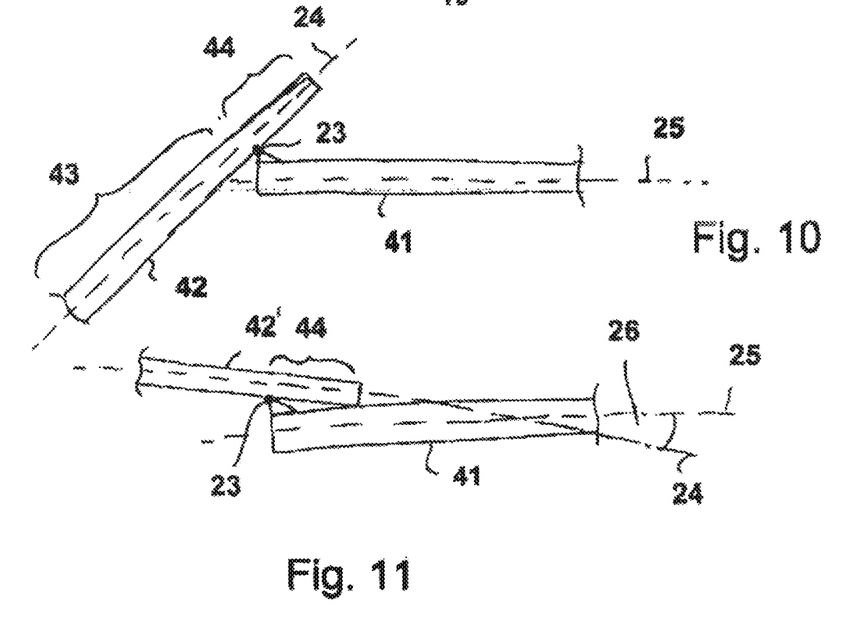
FIG. 10 a further joint of a strut in a first state.
FIG. 11 the joint of FIG. 10 in a second state.

FIG. 10 represents a further embodiment of the invention in which a support element has been omitted, the two sections 41, 42 partly cover one another in the elongated position in the longitudinal direction, with the section 42 having a pivot lever 43 and a support lever 44 at both sides of the bearing point 23 and with the pivot lever 43 projecting beyond the other section 41 and being able to be angled.

In FIG. 11, the arrangement is shown with the two sections 41, 42 in a maximally elongated position, with the section 42' pivoted with respect to FIG. 10 being shown in the maximally overelongated position. The support lever 44 is supported against the section 41 in this position. A further overelongation of the strut which has the two sections 41, 42 is thus prevented.

It is important for such an embodiment of a joint that the longitudinal axis 24, 25 or the pivot planes of the two sections 42, 41 are located in the same plane or in parallel planes which are only minimally offset with respect to one another.

Figure 12:
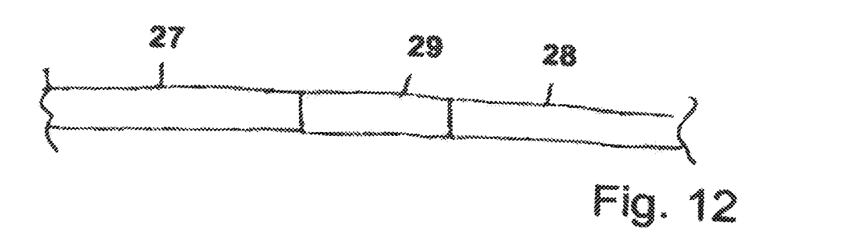
FIG. 12 a joint of a strut which is provided in a joint section at which two sections are arranged at the end face.

In FIG. 12, a strut having two sections 27, 28 which are connected to one another by a joint section 29 is shown schematically.

Figure 13:
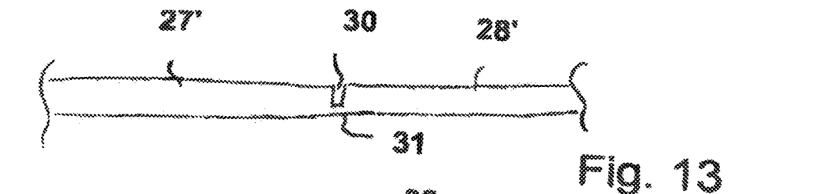
FIG. 13 a film hinge of a strut in a first state.

FIG. 13 shows in more specific form a cut-out 30 in the form of a slit or incision which is introduced into the strut between the sections 27', 28'.

Figure 14:
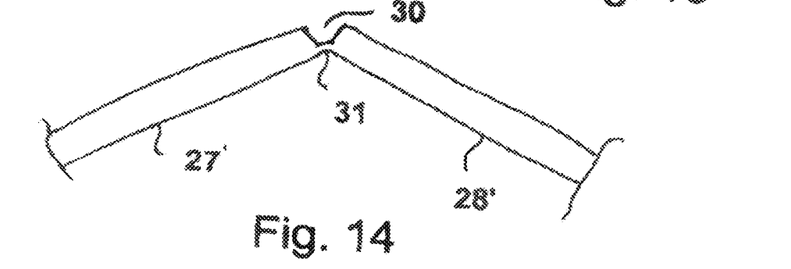
FIG. 14 the film hinge of FIG. 13 in a second state.

FIG. 14 shows the strut of FIG. 13 in a kinked arrangement of the sections 27', 28', with the film hinge 31 lying on the inner side of the strut and the cut-out 30 on its outer side. The sections 27', 28' thus include a smaller angle on the inner side than on the outer side when the strut is angled.

In the elongated state of the strut, the sections on the inner side have an angle which amounts to a maximum of 180°, or only a little above it, for example to a maximum of 190°.

Figure 15:
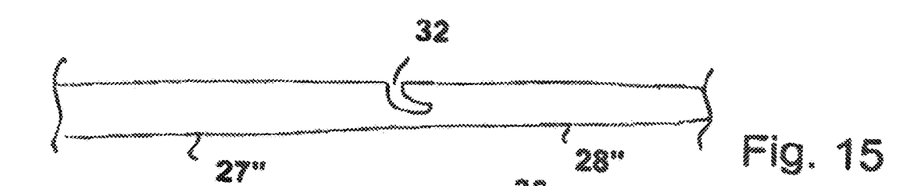
FIG. 15 a further embodiment of a film hinge.

In FIG. 15, another form of the cut-out 32 is shown which does not follow a straight cut, but rather a more complicated shape and which thus provide a longer and more flexible film hinge. Such a complex cut-out 32 can be introduced, for example, by means of laser cutting or etching techniques or other erosive processing techniques.

Figure 16:
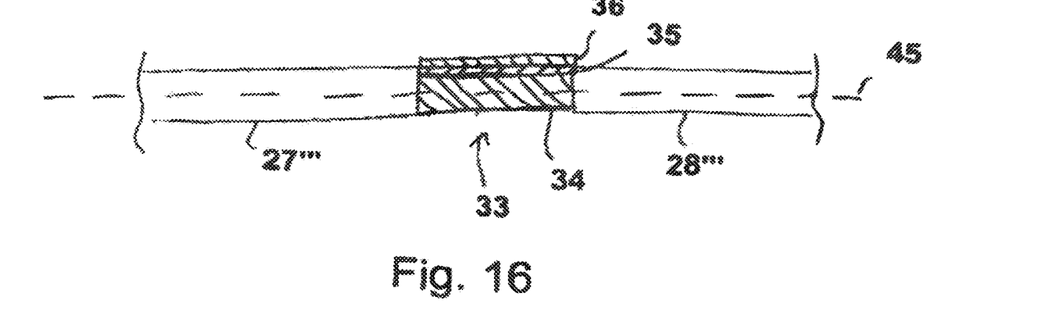
FIG. 16 the embodiment of a joint section at a strut.

FIG. 16 represents another alternative in the formation of a joint at a strut. In FIG. 16, the joint section between two sections 27" and 28" is marked by 33. This joint section 32 has a material 34 on the inner side which can also extend over the center plane 45 of the corresponding strut up to the outer side of the strut which extends perpendicular to the plane of the drawing.

A layer 35 is advantageously provided at the outer side of the strut, said layer being harder than the material 34 and above all being incompressible so that the strut cannot be angled toward the outer side and the overelongation of the strut is already prevented by the property of the material of the part 35. The material 34 is advantageously easily compressible, but solid.

In addition, a layer 36 is shown in FIG. 16 which can likewise be attached to the outer side of the strut instead of the layer 35, or additionally thereto, but is stretchable just like the material of the layer 35 so that, on the one hand, a kinking of the sections 27", 28" toward the inner side of the strut is allowed, a kinking of the sections toward the outer side is, however, limited.

A simple compressibility of a rotor for a fluid pump is achieved by the design in accordance with the invention of conveying blades or of a rotor for a fluid pump having the corresponding joints so that the conveying blades can be brought into the compressed state completely without counter-forces or with small elastic counter-forces and can also be erected again after being brought to the operating site. The described joints are of simple design, are simple to manufacture and are reliable and give the corresponding conveying blades a high flexibility.

The invention claimed is:

1. A compressible rotor for a blood pump, the rotor comprising:
   a hub; and
   at least one conveying blade fastened to the hub,
   wherein the at least one conveying blade comprises a plurality of struts,
   wherein each strut of the plurality of struts has at least one joint,
   wherein the at least one joint comprises a bearing that pivotably connects a first section of a strut to a second section of the strut such that a pivot lever portion of the first section is disposed on a first side of the bearing and a support lever portion of the first section is disposed on a second side of the bearing,
   wherein the bearing permits:
      (a) the first section of the strut to pivot relative to the second section of the strut in a first direction from an overelongated position of the strut to a kinked position of the strut, and
      (b) the first section of the strut to pivot relative to the second section of the strut in a second direction from the kinked position of the strut to the overelongated position of the strut,
   wherein, in the overelongated position, the first section and the second section partially overlap such that the support lever portion of the first section contacts the second section thereby preventing further pivoting of the first section relative to the second section in the second direction.

2. The rotor of claim 1, wherein the bearing is fastened to an end of the second section of the strut.

3. The rotor of claim 1, wherein the bearing of each strut permits the first section to pivot relative to the second section of each strut in a first movement plane.

4. The rotor of claim 1, wherein the pivoting of the first and second sections permit the at least one conveying blade to fold in upon the hub.

5. The rotor of claim 1, wherein the at least one joint is configured such that, from a position where the first section and the second section extend along parallel axes, pivoting of the first section relative to the second section is more limited in the second direction than in the first direction.

6. The rotor of claim 1, wherein the first direction is a direction of rotation of the at least one conveying blade during operation.

7. The rotor of claim 1, wherein the at least one joint bounds angling of the first and second sections beyond an elongation angle in the second direction.

8. The rotor of claim 7, wherein the elongation angle is from 175° to 185°.

9. The rotor of claim 1, wherein the plurality of struts are configured to pivot from an expanded state to a radially compressed state.

10. The rotor of claim 1, wherein the plurality of struts are arranged parallel to one another or in fan shape starting from a common base.

11. The rotor of claim 10, wherein the base is a point.

12. The rotor of claim 10, wherein the base is an arc segment.

13. The rotor of claim 1, wherein the first section of the strut and the second section of the strut can be angled in opposite directions.

14. The rotor of claim 1, wherein the second section of each of the struts is pivotally connected to the hub at a common base.

15. The rotor of claim 1, wherein the at least one conveying blade comprises a membrane held by the plurality of struts.

* * * * *